United States Patent

Ciceri et al.

[11] Patent Number: 5,741,515
[45] Date of Patent: Apr. 21, 1998

[54] KETOPROFEN LIPOSOMES

[75] Inventors: Silvana Ciceri, Como, Italy; Hans-Jürgen Hamann, Dormagen, Germany; Ingrid Hürner, Düsseldorf, Germany; Peter Kurka, Hilden, Germany; Joachim Maasz, Granger, Ind.

[73] Assignee: Bayer Aktiengesellschaft, Leverkusen, Germany

[21] Appl. No.: 542,752

[22] Filed: Oct. 13, 1995

[30] Foreign Application Priority Data

Oct. 20, 1994 [IT] Italy .................. MI94A2142

[51] Int. Cl.$^6$ .................................................. A61K 9/127
[52] U.S. Cl. .................. 424/450; 514/825; 514/886; 514/887
[58] Field of Search .................. 424/450, 401; 514/825, 886, 887

[56] References Cited

U.S. PATENT DOCUMENTS 4,619,794 10/1986 Hauser .................... 264/4.1
4,708,861 11/1987 Popescu .................... 424/1.1
5,008,109 4/1991 Jin .......................... 424/422

FOREIGN PATENT DOCUMENTS 0056781 7/1982 European Pat. Off. .
0249561 12/1987 European Pat. Off. .
2041871 9/1980 United Kingdom .

OTHER PUBLICATIONS

C.P. Jain, et al., Journal of Microencapsulation, vol. 12, No. 4, pp. 401–407, (1995).

H.E. Junginger, et al., Cosmetics & Toiletries, vol. 106, pp. 45–50, (1991).

K. Kriwet, et al., Die Pharmazie, vol. 49, No. 2/3, pp. 187–191, (1994).

Primary Examiner—Gollamudi S. Kishore
Attorney, Agent, or Firm—Sprung Kramer Schaefer & Briscoe

[57] ABSTRACT

The present invention relates to a ketoprofen liposome gel and a process for its preparation which is distinguished by a simple method of preparation by spontaneous formation of liposomes from phospholipids and ketoprofen.

7 Claims, No Drawings

KETOPROFEN LIPOSOMES

The present invention relates to a ketoprofen liposome gel and a process for its preparation which is distinguished by a simple method of preparation by spontaneous formation of liposomes from phospholipids and ketoprofen.

Ketoprofen is a pharmaceutically active substance from the non-steroidal antirheumatic group of the arylpropionic acid type. The non-steroidal antirheumatics are applied both internally and externally for the therapy of inflammations, the lipophilic representatives of this class of active compound being particularly suitable for topical application. A problem in the application of pharmaceutical substances is, for many pharmaceutical substances, the poor penetrability of the skin so that often the therapeutic level necessary in the tissue is not reached. It is therefore frequently attempted by inclusion of the active compounds in liposomes to improve the penetrability into the tissue through the stratum corneum.

Liposomes are formed from phospholipids which are arranged together in one or more concentric layers to give spherical liquid-crystalline particles. The size of liposomes varies depending on the manner of preparation and type from about 80 nm to 100 µm. Liposomes are classified by their size and by the number of the phospholipid layers, differentiation being made between unilamellar and multilamellar, possibly only oligolamellar.

Phospholipids are amphiphilic substances, i.e. they possess both a hydrophilic molecular moiety, mostly a phosphoric acid ester substituted by a quaternary ammonium compound, and a lipophilic molecular moiety which mostly consists of saturated and unsaturated fatty acids. As a result of these properties there is, as with all surfactants, the tendency to be arranged together in aqueous systems to give associates in order to decrease the energy of the system. Phospholipids tend to be arranged together to give bilayers, the lipophilic molecular moieties being oriented towards one another and these bilayers being separated by aqueous compartments. These bilayers can then be arranged concentrically to give spherical structures, liposomes. Liposomes consist either of one or more phospholipid bilayers, in which either hydrophilic substances are intercalated in the aqueous compartments, or lipophilic substances in the bilayers.

Since the phospholipids from which liposomes are formed in some cases correspond to the physiological membrane lipids and lipid substances of the horny layer or are very similar to these, topical liposomes, in particular, are credited with a greater penetrability through the skin. This is the case, in particular, for inflamed skin, into which liposomes can penetrate readily (H. E. Junginger et al. Cosm. Toiletr. 45–50, 1991).

Niosomes are vesicles of the same structure as the liposomes which, however, are formed from non-ionic amphiphiles, such as polyoxyethylenes etherified or esterified with fatty acids or, for example, fatty acid sucrose diesters.

Various attempts have already been made to prepare liposome formulations even from non-steroidal antirheumatics, but a high energy expenditure always has to be used in this preparation process in order to achieve an adequate particle size or organic solvents or detergents have to be employed which subsequently have to be removed from the formulation again. An example of this is offered by EP 0,249,561, wherein methods and putting together of formulations in which non-steroidal antirheumatics are included in liposomes are described. The patent claims liposomes for oral administration and liposomes which are resistant to gastric juice, the process for the preparation of these liposomes, however, corresponds to the customary methods, i.e. the phospholipids are dissolved in an organic phase which subsequently has to be removed again.

1. Hydration method

A phospholipid mixture is evaporated in a glass flask so that a thin lipid film forms on the wall. This film is then moistened with a buffer solution and shaken, liposomes spontaneously forming. Critical parameters in this process are the lipid film thickness, the volume of buffer solution and the duration and intensity of the motion. The mostly multilamellar liposomes formed in this process can be additionally further reduced in size by ultrasound or the so-called French press.

2. Ultrasound method

The phospholipids are dispersed in water and then comminuted by mechanical stress, in this case ultrasound. Alternatively, the liposomes can also be prepared from dispersions by pressure stress in a suitable extruder (French press).

3. Solvent injection method

The phospholipids are dissolved in a suitable organic solvent (ether, methanol and mixtures) and this solution is injected into warm water in which the substance to be included is dissolved. After stripping off the solvent in vacuum, mostly unilamellar vesicles are formed.

4. Detergent method

An aqueous mixed micelle solution of phospholipids, a detergent and the substance to be included is prepared and the detergent is subsequently removed by dialysis, column chromatography or other suitable processes.

5. Reverse phase evaporation method

A water-in-oil emulsion is prepared in an excess of the organic phase using a buffer, the phospholipids and the substances to be included and the organic phase is then evaporated in vacuum. At the end of the evaporation process, a phase inversion occurs and a suspension of large unilamellar liposomes is formed.

In their technical implementation, these methods are each associated either, in the case of mechanical preparation of the liposomes, with a high energy expenditure, or, in the case of the methods using solvents or detergents, with a high expenditure on purification of the product. There is therefore the wish for a simple preparation of such systems.

Surprisingly, it has been found that ketoprofen liposomes can be prepared extremely simply by mixing ketoprofen with phospholipids at pHs of above 6, preferably 6 to 8, and subsequent pH reduction to values below 6, preferably 4 to 6. Owing to the deprotonated carboxyl group, the sodium salt of ketoprofen has armphiphilic character and is arranged together with the phospholipids, and mixed micelles of the phospholipid employed and the ketoprofen salt are formed. The free acid still present, ketoprofen, is incorporated into these mixed micelies. On dilution of this alkaline mixed micelle solution with a suitable buffer solution, the pH of the solution is reduced to a value below 6 and the proportion of deprotonated ketoprofen is decreased. As a result the mixed micelle membrane is destabilized and spontaneous formation of liposomes occurs. In this process it is in particular crucial that organic solvents (reverse phase evaporation method) or detergents which have to be removed from the formulation (detergent removal method) or energy-expensive comminution methods (hydration method, sonication method, French press etc.) do not have to be used as in many other preparation processes for liposomes. The formulation contains both the corresponding salt of the ketoprofen and the free acid, ketoprofen. The particle sizes are in the range from 80 to 200 nm.

Suitable phospholipids are the natural phospholipids, sphingolipids, glycosphingolipids, and also synthetic phospholipids such as dipalmitoylphospatidylcholine—, —serine or—ethanolamine-glycerol or the corresponding oleic acid esters of these compounds.

Particularly suitable are natural and synthetic phospholipids which correspond to the general formula (I)

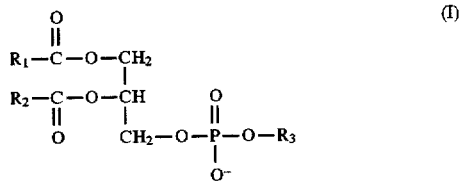

and their mixtures, where $R_1$ and $R_2$ denote alkyl radicals and/or mono- to tetraunsaturated alkenyl groups having 10 to 23, preferably 13 to 21, C units and $R_3$ is derived from the following group:

—OH,
—$CH_2CH_2N^+(CH_3)_3$,
—$CH_2CH_2NH_3^+$,
—$CH_2CHNH_3^+COO^-$,
—$CH_2CHOHCH_2OH$,
—$HC_6H_5(OH)_5$.

Suitable non-ionic amphiphiles are especially polyoxyethylenes esterified or etherified with fatty acids and sucrose diesters which are suitable for the formation of niosomes.

Preferred non-ionic amphiphiles are compounds of the formulae

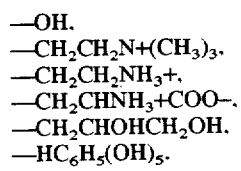

and

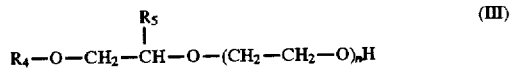

where $R_4$ and $R_5$ are identical or different and in each case represent alkyl or alkenyl having 12 to 16 C atoms and n represents a number from 3 to 25.

Suitable gel formers are hydrogel formers known to the person skilled in the art, such as derivatized celluloses, polyvinylpyrrolidones, polyacrylates and other synthetic hydrocolloids, and also natural gel formers such as agar, gums, glycans, alginates, gelatins and other polysaccharide and protein hydrocolloids and block copolymers of polyoxyethylene and polyoxypropylene.

Customary auxiliaries which may be mentioned in particular are preservatives, antioxidants, colourants and other substances which are used for the microbial and chemical stabilization of the formulation.

Ketoprofen liposome gels according to the invention are prepared e.g. by incorporating ketoprofen phospholipid mixed micelles in certain hydrogels. To do this, ketoprofen is first dissolved in 1N NaOH solution and a mixed micelle dispersion is prepared in this medium by incorporation of a phospholipid, in particular of the formula (I). Suitable phospholipids are natural and synthetic phospholipids which can contain unsaturated and saturated fatty acids (example Phospholipon® E 90 purified soybean lecithin, Lipoid® E 80 purified egg yolk lecithin, Lipoid® E 100 purified egg yolk lecithin, Lipoid® S 100 purified soybean lecithin, Lipoid® E PC purified egg yolk lecithin, Epikuron® 200 SH purified hydrogenated soybean lecithin).

In the following Examples, CREMOPHOR®RH40 is a polyoxyl -40- hydrogenated castor oil.

EXEMPLARY EMBODIMENTS

Example 1

Preparation of the mixed micelle solution

| Ketoprofen | 18.62 g |
| Phospholipon ® 90 purified soybean lecithin | 17.11 g |
| 1 N NaOH solution | 100.0 g |

Ketoprofen is dissolved in the sodium hydroxide solution. The solution is then heated to 90° C., and the phospholipid is dispersed in it over the course of 90 minutes. A clear yellow mixed micelle dispersion having a pH above 6 is formed.

The mixed micelle solution is incorporated in the following hydrogel:

| Lutrol ® F 127 | 18.00% |
| Buffer solution pH 5 | 63.58% |
| Cremophor ® RH 40 | 5.00% |
| Mixed micelle dispersion | 13.42% |

By diluting the mixed micelle solution with the hydrogel a stable ketoprofen liposome gel is formed. The concentration of ketoprofen in the gel is 2.5%.

Example 2

The mixed micelle solution from Example 1 is incorporated in the following hydrogel:

| Polyacrylic acid | 1.00% |
| Buffer solution pH 5 | 80.33% |
| Cremophor ® RH 40 | 5.00% |
| Mixed micelle dispersion | 13.42% |

By diluting the mixed micelle solution with the hydrogel a stable ketoprofen liposome gel is formed. The concentration of ketoprofen in the gel is 2.5%.

We claim:

1. A process for the preparation of ketoprofen liposomes comprising adding a mixture of ketoprofen and phospholipids or non-ionic amphiphiles to a solution having a pH in the range of 6 to 8, decreasing the pH of the solution to a pH below 6 sufficient to effect spontaneous formation of liposomes, wherein the non-ionic amphiphiles are compounds of formulae (II) and (III)

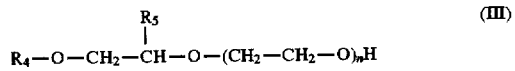

where $R_4$ and $R_5$ are identical or different and in each case represent alkyl or alkenyl having 12 to 16 carbon atoms and n represents a number from 3 to 25.

2. Ketoprofen liposomes prepared according to claim 1.
3. Pharmaceutical preparations containing ketoprofen liposomes prepared according to claim 1.
4. Ketoprofen liposomes according to claim 1, wherein said liposomes are in the form of a liquid or a semisolid.

5. Pharmaceutical preparations containing ketoprofen liposomes according to claim 2 which are composed of phospholipids of the formula (I)

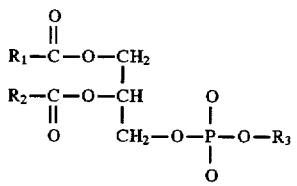

where $R_1$ and $R_2$ denote alkyl radicals and/or mono-to tetraunsaturated alkenyl groups having 10 to 23, preferably 13 to 21, C units and $R_3$ is derived from the following group:

—H,
—$CH_2CH_2N+(CH_3)_3$,
—$CH_2CH_2NH_3{}^+$,
—$CH_2CHNH_3{}^+COO-$,
—$CH_2CHOHCH_2OH$,
—$HC_6H_5(OH)_5$ and their mixtures in combination with ketoprofen and/or ketoprofen sodium mixed micelles.

6. Pharmaceutical preparations according to claim 3 which further include auxiliary compositions selected from the group consisting of preservatives, antioxidants, colourants, microbial stabilizers and chemical stabilizers.

7. Pharmaceutical preparations according to claim 3, wherein the ketoprofen liposomes are incorporated into hydrogels.

* * * * *